United States Patent
Knochel et al.

(10) Patent No.: US 7,015,342 B2
(45) Date of Patent: Mar. 21, 2006

(54) FERROCENYL LIGANDS AND METHOD FOR THE PRODUCTION OF SUCH LIGANDS

(75) Inventors: Paul Knochel, Munich (DE); Matthias Lotz, Munich (DE); Axel Monsees, Frankfurt (DE); Thomas Riermeier, Nidderau-Ostheim (DE); Renat Kadyrov, Frankfurt (DE); Juan Jose Almena Perea, Hanau (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/511,439

(22) PCT Filed: Apr. 17, 2003

(86) PCT No.: PCT/EP03/04054

§ 371 (c)(1),
(2), (4) Date: Jun. 10, 2005

(87) PCT Pub. No.: WO03/093285

PCT Pub. Date: Nov. 13, 2003

(65) Prior Publication Data

US 2005/0240007 A1    Oct. 27, 2005

(30) Foreign Application Priority Data

Apr. 30, 2002 (DE) .............................. 102 19 490

(51) Int. Cl.
*C07F 17/00* (2006.01)
*B01J 31/00* (2006.01)
*C07C 5/02* (2006.01)

(52) U.S. Cl. .......................... 556/14; 556/28; 556/136; 556/143; 502/154; 502/155; 585/275; 568/862

(58) Field of Classification Search .................. 556/14, 556/28, 136, 143; 502/154, 155; 585/275; 568/862
See application file for complete search history.

(56) References Cited

U.S. PATENT DOCUMENTS 6,191,284 B1 * 2/2001 Knochel et al. ............ 548/402
6,777,567 B1 * 8/2004 Weissensteiner et al. ..... 556/16
6,939,981 B1 * 9/2005 Boaz .......................... 556/14

FOREIGN PATENT DOCUMENTS

DE           199 52 348        6/2000

* cited by examiner

*Primary Examiner*—Porfirio Nazario-Gonzalez
(74) *Attorney, Agent, or Firm*—Oblon, Spivak, McClelland, Maier & Neustadt, P.C.

(57) ABSTRACT

The invention relates to ferrocenyl ligands of general formula (II), the $S_{fc}$,S-enantiomer or the $R_{fc}$,R-enantiomer of the ferrocenyl ligands of formula (II) being enriched, and a method for producing such ligands.

10 Claims, No Drawings

FERROCENYL LIGANDS AND METHOD FOR THE PRODUCTION OF SUCH LIGANDS

The invention relates to selected enantiomerically enriched bidentate organophosphorus ferrocenyl ligands which are particularly useful for enantioselective hydrogenation, and to a process for preparing such ligands.

Trisubstituted bidentate organophosphorus compounds have achieved great importance as ligands in homogeneous catalysis. In particular, the use of bisphosphine catalysts in asymmetric hydrogenation has been known for a long time (Burk et al., Tetrahedron 1994, 4399), with, for example, WO 96/32400 and WO 95/21151 describing the use of ferrocenyl ligands which do not have a $C_2$ symmetry.

However, catalysts comprising the asymmetric ferrocenyl ligands known to date have only limited utility for targeted enantioselective syntheses. On the other hand, DE 199 52 348 makes available a new class of enantiomerically enriched ferrocenyl ligands having the general formula

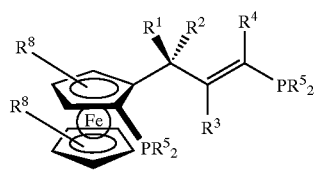

(I)

which have proven to be catalyst ligands having a good enantioselective effect, especially in asymmetric homogeneous catalytic hydrogenation. However, in terms of industrial use, the search for catalyst ligands which are particularly suitable for asymmetric hydrogenation continues to be of great interest. Likewise, the development of further enantioselective preparative methods giving good yields of such ligands is of great importance in order to ensure the availability of the catalysts for an industrial process.

It was therefore an object of the present invention to provide ferrocenyl ligands which display a very high enantioselectivity in the homogeneously catalyzed asymmetric hydrogenation of unsaturated compounds and can be prepared in adequate amounts and with good enantioselectivity.

This object is achieved by ferrocenyl ligands of the general formula (II) which can be in the form of the $S_{fc}$ diastereomer (IIa) or $R_{fc}$ diastereomer (IIb)

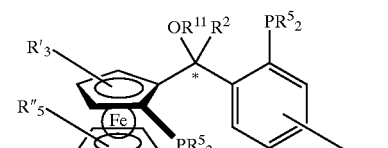

(IIa)

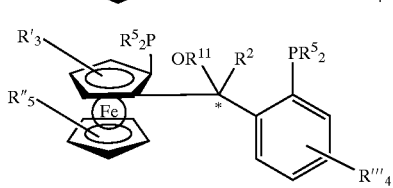

(IIb)

and are selected from the class of compounds described in DE 199 52 348, where the $S_{fc}$,S enantiomer of the formula (IIIa) is present in excess in the mixture (IIa) or the $R_{fc}$,R enantiomer of the formula (IIIb) is present in excess in the mixture (IIb)

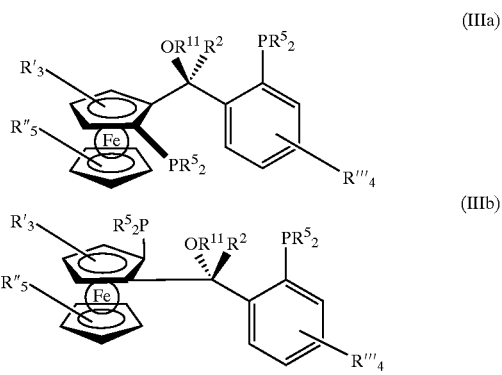

and

R' and R" are radicals which can be selected independently from the group consisting of H and $CH_3$ or can be a linker which connects the ligands to a polymeric support and the radicals R'" are radicals which can be selected independently from the group consisting of H and $(C_1-C_4)$-alkyl and the radicals $R^5$ are each, independently of one another, a $C_6$-aryl, $C_5$–$C_6$-cycloalkyl, adamantyl or $C_1$–$C_4$-alkyl radical which may bear one or more $(C_1-C_4)$-alkyl substituents and $R^2$ is hydrogen or a $(C_1-C_4)$-alkyl radical and $R^{11}$ is a $(C_1-C_4)$-alkyl radical.

As alkyl radicals $R^2$ and $R^{11}$, preference is given to methyl radicals. Particular preference is given to ferrocenyl ligands of the formula (II) in which R', R", R'" and $R^2$ are hydrogen radicals and the radical $R^{11}$ is a methyl radical. The radicals $R^5$ are preferably cyclohexyl, cyclopentyl, adamantyl, isopropyl, tert-butyl radicals and particularly preferably phenyl, tolyl or xylyl radicals.

The ligands claimed can also be fixed to a polymer via a suitable linker R' or R". Typical linkers are, for example, radicals of the formula B-X-Z, where X is a spacer, such as 1,4'-biphenyl, 1-,2-ethylene or 1-,3-propylene and B is a $CR^9$, $NR^9$, O, S, $SiR^9_2$ radical, with $R^9$ being H or $(C_1-C_{18})$-alkyl, and Z is a functional group such as O—, NH—, COO—, CONH—; CH2=CH—, NHCONH—, OCONH— or NHCOO—.

Preference is also given to ferrocenyl ligands of the formula (II) in which the excess $S_{fc}$,S enantiomer or $R_{fc}$,R enantiomer is present in a proportion of more than 60%, preferably more than 75%, particularly preferably more than 90%. The use of stereoisomers having a purity of above 99% is ideal.

It can surprisingly be shown that catalyst complexes containing an excess of ferrocenyl ligand stereomers of the formula (III) display a higher enantioselectivity in the asymmetric hydrogenation of unsaturated compounds than those described explicitly in DE 199 52 348, which are, in particular, present in a form enriched in the $S_{fc}$,R enantiomer. The preparative method described there gives ferrocenyl ligands in which it is the $S_{fc}$,R enantiomer or the $R_{fc}$,S enantiomer which is present in excess.

The ferrocenyl ligands claimed, in which the $S_{fc}$,S enantiomer or the $R_{fc}$,R enantiomer is present in excess, can be prepared by the general synthesis described below. It is particularly advantageous here that the $S_{fc},S$ enantiomer or the $R_{fc},R$ enantiomer is formed in excess without a further enrichment step.

Such a process is described below using the synthesis of the $S_{fc},S$ enantiomers as an example. In the first step of the preparation, a ferrocene is converted into the chiral ferrocenyl sulfoxide 1 by a method of Kagan et al. (*J. Org. Chem.* 1995, 60, 2502). To introduce the aromatic group and the first phosphorus-containing group, the ferrocenyl ring is lithiated in the presence of a lithium base and transmetallated. Coupling to form the corresponding compound 2 takes place in the presence of a metal catalyst of transition group 8, in particular a rhodium catalyst, forming the stereoisomer 2a in excess.

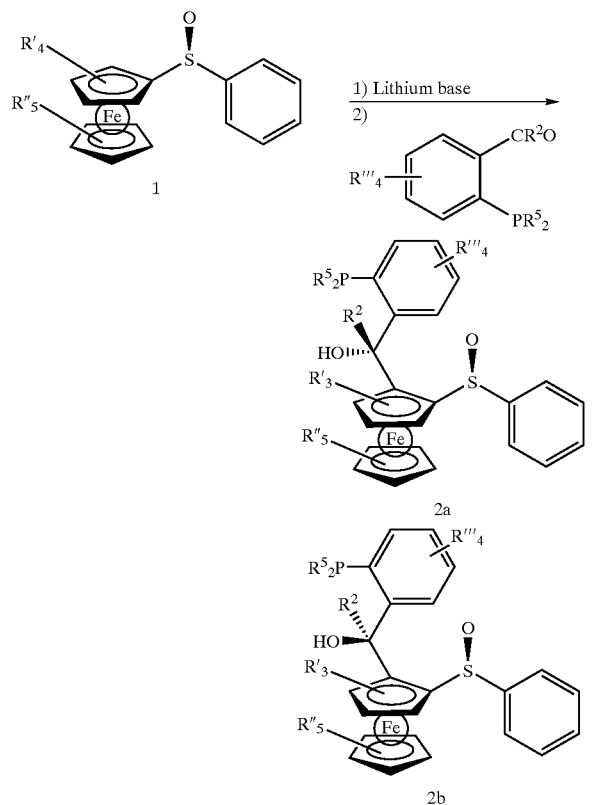

The mixture of enantiomers obtained can either be processed further directly or, in an alternative embodiment, firstly be separated and subsequently processed further. The reaction schemes are illustrated below for the reaction of the enantiomer 2a. After addition of an alkali metal hydride, e.g. KH, the compound 2a is subsequently reacted with the corresponding iodide to form the compound 3a.

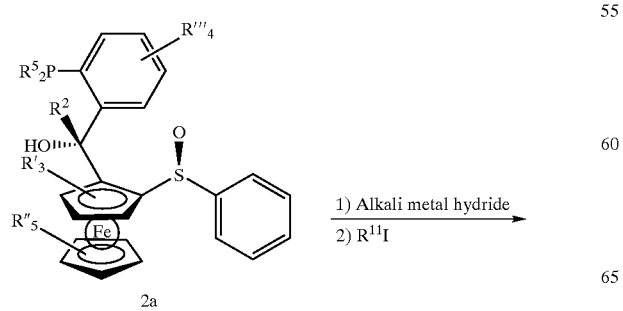

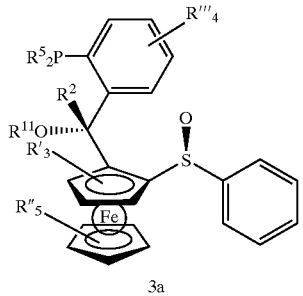

The sulfoxide group can be replaced by the second phosphorus-containing group in the presence of a strong lithium base. This gives the ligand according to the invention, with the $S_{fc},S$ enantiomer 4a being present in excess.

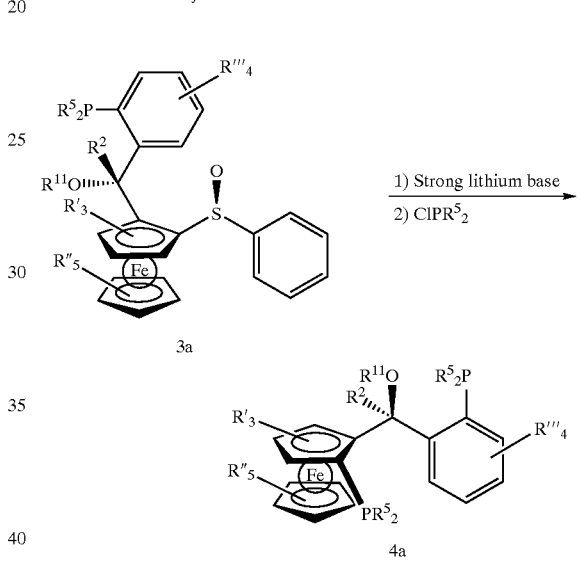

The compound 2b is converted into the corresponding compounds 3b and 4b. The enantiomeric purity of the synthesis can be increased further by separation of the diastereomers 2a and 2b and/or the diastereomers 3a and 3b.

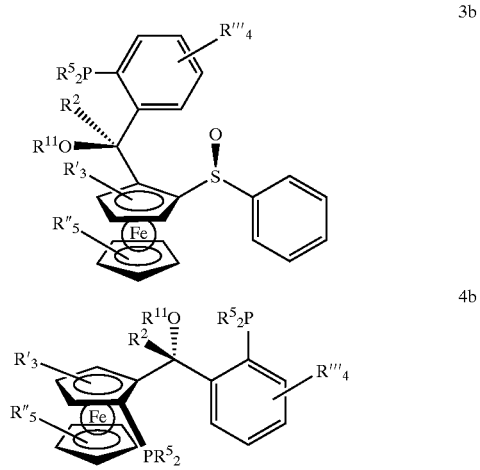

The process described provides a direct route to diastereomer mixtures which have a high proportion of $S_{fc},S$ enantiomers and can be used directly as ligands for catalysts. An even higher excess of the $S_{fc},S$ enantiomer can be achieved by further purification, e.g. by means of chromatographic methods.

The use of the R enantiomer as starting material correspondingly leads to the enantiomeric $R_{fc},R$ product in excess.

The process described can be utilized not only for the enantioselective synthesis of the ligands which are particularly useful for asymmetric hydrogenation but is also suitable for the synthesis of ferrocenyl ligands of the general formula (II), with the $S_{fc},S$ enatiomer or the $R_{fc},R$ enantiomer of the formula (III) being present in excess.

The present invention thus further provides a process for preparing $S_{fc}$- or $R_{fc}$-ferrocenyl ligands of the formula (II),

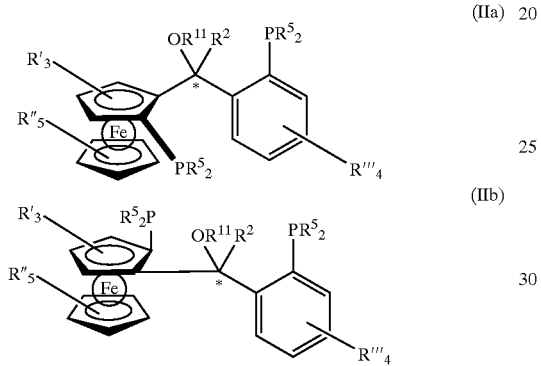

(IIa)

(IIb)

where the $S_{fc},S$ enantiomer of the formula (IIIa) is present in excess in the mixture (IIa) or the $R_{fc},R$ enantiomer of the formula (IIIb) is present in excess in the mixture (IIb)

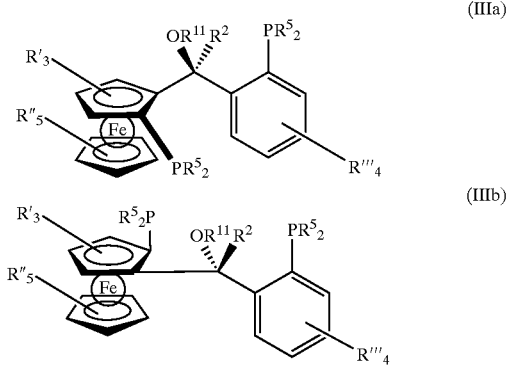

(IIIa)

(IIIb)

and

R' and R" can each be, independently of one another, a substituent selected from the group consisting of H and $(C_1-C_4)$-alkyl or a linker which connects the ligands to a polymeric support and the radicals R''' can be selected independently from the group consisting of H, $(C_1-C_{18})$-alkyl, $(C_1-C_{18})$-alkoxy, $(C_1-C_{18})$-acyloxy, $(C_6-C_{14})$-aryl, $(C_3-C_{18})$-heteroaryl, $(C_2-C_{17})$-heteroalkyl, $(C_3-C_8)$-cycloalkyl and $(C_2-C_{10})$-alkenyl, where two adjacent radicals may also be joined to one another to form a ring system, and the radicals $R^5$ can each be, independently of one another, $(C_1-C_{18})$-alkyl, $(C_6-C_{18})$-aryl, $(C_6-C_{18})$-aryl-$(C_1-C_8)$-alkyl, $(C_3-C_{18})$-heteroaryl, $(C_3-C_{18})$-heteroaryl-$(C_1-C_8)$-alkyl, $(C_2-C_{17})$-heteroalkyl, $(C_3-C_8)$-cycloalkyl, $(C_3-C_8)$-cycloalkyl-$(C_1-C_8)$-alkyl, $(C_2-C_{10})$-alkenyl radicals which may bear one or more $(C_1-C_4)$-alkyl substituents and the radical $R^2$ is H or a $(C_1-C_8)$-alkyl radical, $(C_6-C_{18})$-aryl, $(C_6-C_{18})$-aryl-$(C_1-C_8)$-alkyl radical and the radical $R^{11}$ can be a $(C_1-C_{18})$-alkyl, $(C_6-C_{18})$-aryl, $(C_6-C_{18})$-aryl-$(C_1-C_8)$-alkyl radical which comprises the process steps:
a) coupling of a chiral ferrocenyl sulfoxide with an aromatic aldehyde of the formula (IV),

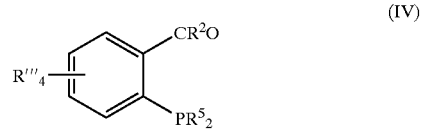

(IV)

with the chiral ferrocenyl sulfoxide being lithiated in the presence of a lithium base and the coupling of the aromatic aldehyde subsequently being carried out by transmetallation in the presence of a metal catalyst of transition group 8, b) coupling of the free OH group on the chiral center of the reaction product from step a) with an organic radical $R^{11}$ by addition of a halide $R^{11}Hal$, preferably the iodide $R^{11}I$, in the presence of an alkali metal hydride, c) replacement of the sulfoxide group of the reaction product from step b) in the presence of a strong lithium base by a phosphorus halide of the formula $HalPR^5_2$, preferably by a phosphorus chloride $ClPR^5_2$.

The process described is preferably used for preparing ligands whose radicals R', R", R''' are, independently of one another, H and/or $CH_3$. The radicals $R^5$ are preferably, independently of one another, $C_6$-aryl-, $(C_5-C_6)$-cycloalkyl-, adamantyl or $(C_1-C_4)$-alkyl radicals. $R^2$ is preferably H or a $(C_1-C_4)$-alkyl group and $R^{11}$ is preferably a $(C_1-C_4)$-alkyl group.

The ligands claimed can be reacted simply with metals to form the corresponding complexes. The claimed ligands in complexed form are typically used in the asymmetric hydrogenation of unsaturated compounds, in which case they are reacted with metals to form complexes which can be used as catalysts. The catalysts can either be formed directly as intermediates in a one-pot reaction by simply combining the ligand according to the invention and metal, metal salt or metal precomplex or else can be prepared and isolated beforehand and added as finished complex to the reaction mixture. As coordination center, it is possible to employ, in particular, the metals of transition groups 7 and 8, preferably Co, Ni, Ru, Pd, Ir, Pt, particularly preferably Rh, forming complexes which contain at least one ligand according to the invention. In addition, further ligands originating, for example, from the precomplex, the solvent or another addition to the reaction can be present in the complex.

Examples of metal salts which are suitable for preparing the complexes are metal chlorides, bromides, iodides, cyanides, nitrates, acetates, acetylacetonates, hexafluoroacetylacetonates, tetrafluoroborates, perfluoracetates or triflates, in particular of palladium, platinum, rhodium, ruthenium, iridium, cobalt dr/and nickel.

Examples of suitable precomplexes are:

cyclooctadienepalladium chloride, cyclooctadienepalladium iodide, 1,5-hexadienepalladium chloride, 1,5-hexadienepalladium iodide, bis(dibenzylideneacetone)palladium, bis(acetonitrile)palladium(II) chloride, bis(acetonitrile)palladium(II) bromide, bis(benzonitrile)palladium(II) chloride, bis(benzonitrile)palladium(II) bromide, bis(benzonitrile)palladium(II) iodide, bis(allyl)palladium, bis(methallyl)palladium, allylpalladium chloride dimer, methallylpalladium chloride dimer, tetramethylethylenediaminepalladium dichloride, tetramethylethylenediaminepalladium dibromide, tetramethylethylenediaminepalladium diiodide, tetramethylethylenediamine(dimethyl)palladium, cyclooctadieneplatinum chloride, cyclooctadieneplatinum iodide, 1,5-hexadieneplatinum chloride, 1,5-hexadieneplatinum iodide, bis(cyclooctadiene)platinum, potassium (ethylenetrichloroplatinate), cyclooctadienerhodium(I) chloride dimer, norbornadienerhodium(I) chloride dimer, 1,5-hexadienerhodium(I) chloride dimer, tris(triphenylphosphine)rhodium(1) chloride, hydridocarbonyltris(triphenylphosphine)rhodium(I) chloride, bis(cyclooctadiene)rhodium(I) perchlorate, bis(cyclooctadiene)rhodium(I) tetrafluoroborate, bis(cyclooctadiene)rhodium(I) triflate, bis(acetonitrilecyclooctadiene)rhodium(I) perchlorate, bis(acetonitrilecyclooctadiene)rhodium(I) tetrafluoroborate, bis(acetonitrilecyclooctadiene)rhodium(I) triflate, cyclopentadienerhodium(III) chloride dimer, pentamethylcyclopentadienerhodium(III) chloride dimer, (cyclooctadiene)Ru($\mu^3$-allyl)$_2$, ((cyclooctadiene)Ru)$_2$(acetate)$_4$, ((cyclooctadiene)Ru)$_2$(trifluoroacetate)$_4$, RuCl$_2$(arene) dimer, tris(triphenylphosphine)ruthenium(II) chloride, cyclooctadieneruthenium(II) chloride, cyclooctadieneiridium(I) chloride dimer, bis(cyclooctene)iridium(I) chloride dimer, bis(cyclooctadiene)nickel, (cyclododecatriene)nickel, tris(norbornene)nickel, nickel tetracarbonyl, nickel(II) acetylacetonate.

The present invention further provides for the use of the ferrocenyl ligands claimed and the catalysts comprising such ligands for the asymmetric hydrogenation of unsaturated organic compounds. Such catalysts display a relatively high enantioselectivity.

The complexes according to the invention are particularly useful in the asymmetric hydrogenation of C=C, C=O or C=N bonds, in which they display high activities and selectivities, and also in asymmetric hydroformylation.

EXAMPLES

Example 1

Preparation of Individual Compounds of the Formula (2a) and (2b)

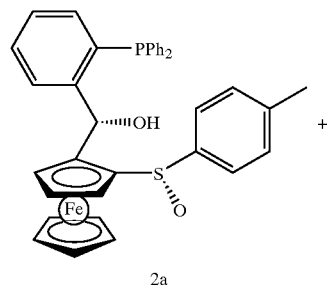

2a

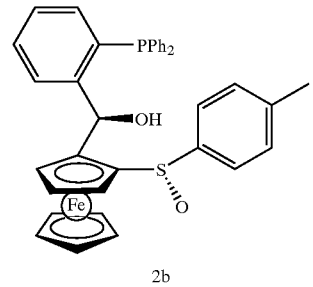

2b

In a 100 ml round-bottomed flask provided with an argon inlet, (S)-ferrocenyl p-tolyl sulfoxide (1) (1.78 g, 5.49 mmol) was dissolved in THF (40 ml) and the solution was cooled to −78° C. Lithium diisopropylamine solution (3.30 ml, 6.59 mmol; 2.0 M in THF) was subsequently added slowly. After stirring at −78° C. for 60 minutes, 2-(diphenylphosphino)benzaldehyde (2.08 g, 7.14 mmol) dissolved in THF (5 ml) was added dropwise and the reaction solution was stirred at −78° C. for one hour. After stirring overnight at room temperature, it was quenched with saturated NH$_4$Cl solution (20 ml), the organic phase was separated off and the aqueous phase was extracted with CH$_2$Cl$_2$ (2×50 ml). The combined organic phases were washed with NaCl solution (20 ml), dried over MgSO$_4$, filtered and the solvent was distilled off on a rotary evaporator. The crude product was purified by column chromatography (n-pentane/diethyl ether 2:1). The alcohol 2a (1.32 g, 2.14 mmol, 39%) (m.p.: 159° C.) and the alcohol 2b (0.99 g, 1.61 mmol, 29%) were obtained as yellow solids. In addition, part of the sulfoxide 1 used could be recovered (429 mg, 1.32 mmol, 24%).

2a:

[α]D$^{20}$=+465.20 (c=0.87, CHCl$_3$).

IR (KBr): 3436 (br, vs), 3053 (m), 2922 (m), 1634 (m), 1435 (m), 1045 (m), 1011 (m), 810 (m), 745 (m), 696 (m), 505 (m).

$^1$H-NMR (CDCl$_3$, 300 MHz): 7.92–7.88 (m, 1H), 7.41–7.37 (m, 3H), 7.19–6.75 (m, 14H), 6.20 (d, J=0.6 Hz, 1H), 5.91 (d, J=7.8 Hz, 1H), 4.49 (s, br, 6H), 3.82–3.80 (m, 1H), 3.12–3.11 (m, 1H), 2.27 (s, 3H).

$^{13}$C-NMR (CDCl$_3$, 75 MHz): 146.57 (d, J=23.3 Hz), 140.54 (d, J=11.7 Hz), 137.10 (d, J=11.7 Hz), 136.11 (d, J=11.6 Hz), 134.91–132.84 (m), 129.79, 128.93–126.80 (m), 124.08, 94.37, 88.75, 74.75 (d, J=2.9 Hz), 70.40, 70.16, 66.76, 65.16 (d, J=30.4 Hz), 21.35.

$^{31}$P-NMR (CDCl$_3$, 81 MHz): −17.26.

MS (EI): 614 (M$^+$, 9), 598 (46), 597 (42), 533 (33), 475 (11), 459 (19), 398 (19), 353 (43), 337 (100), 308 (33), 290 (29), 261 (51), 183 (53), 124 (51), 91 (56), 77 (14), C$_{36}$H$_{31}$FeO$_2$PS (614.53): HR-MS: calc.: 614.1132. found.: 614.1137.

2b:

IR (KBr): 3436 (br, vs), 3053 (m), 2923 (m), 1636 (m), 1435 (s), 1026 (s), 1011 (m), 810 (m), 745 (s), 697 (s), 503 (s).

$^{31}$P-NMR (CDCl$_3$, 81 MHz): −14.77.

MS (EI): 614 (M$^+$, 11), 598 (75), 597 (46), 533 (70), 475 (15), 459 (53), 398 (33), 353 (46), 337 (100), 306 (19), 259 (23), 183 (32), 124 (56), 91 (64), 77 (19). C$_{36}$H$_{31}$FeO$_2$PS (614.53): HR-MS: calc.: 614.1132. found.: 614.

Example 2

Preparation of a Compound of the Formula (3a)

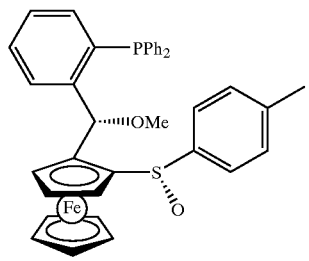

3a

In a 50 ml round-bottomed flask provided with an argon inlet, KH (41 mg, 1.02 mmol) was suspended in THF (1 ml) and cooled to 0° C. The alcohol 2a from Ex. 1 (482 mg, 0.78 mmol) dissolved in THF (9 ml) was subsequently slowly added dropwise at 0° C. and the reaction mixture was stirred at room temperature for 1 hour. It was once again cooled to 0° C. and MeI (122 mg, 0.86 mmol) was added dropwise. After stirring at 0° C. for 10 minutes and at room temperature for 30 minutes, the reaction mixture was quenched with saturated $NH_4Cl$ solution (20 ml), the organic phase was separated off and the aqueous phase was extracted with $CH_2Cl_2$ (2×50 ml). The combined organic phases were washed with NaCl solution (20 ml), dried over $MgSO_4$, filtered and the solvent was distilled off on a rotary evaporator. The crude product was purified by column chromatography (n-pentane/$Et_2O$ 1:1, then $Et_2O$). The methyl ether 3a (355 mg, 0.56 mmol, 72%) was obtained as a yellow solid (m.p.: 98–100° C.).

$[\alpha]D^{20}$=−28.20 (c=0.61, $CHCl_3$).

IR (KBr): 3053 (m), 2925 (m), 1631 (m), 1435 (m), 1087 (s), 1042 (s), 817 (m), 746 (s), 697 (s), 545 (m), 500 (s).

$^1$H-NMR ($CDCl_3$, 300 MHz): 7.53–7.50 (m, 2H), 7.46–7.42 (m, 1H), 7.27–7.09 (m, 14H), 7.00–6.95 (m, 1H), 6.17 (d, J=7.2 Hz, 1H), 4.14 (s, 5H), 3.99–3.97 (m, 1H), 3.85–3.84 (m, 2H), 3.17 (s, 3H), 2.30 (s, 3H).

$^{31}$P-NMR ($CDCl_3$, 81 MHz): −17.45.

MS (EI): 628 (M$^+$, 16), 612 (11), 563 (31), 531 (22), 489 (8), 459 (11), 353 (45), 337 (100), 261 (4), 183 (24), 121 (11), 91 (13). $C_{37}H_{33}FeO_2PS$ (628.55): HR-MS: calc.: 628.1288. found.: 628.1306.

Example 3

Preparation of a Compound of the Formula (3b)

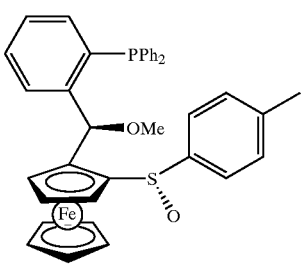

3b

In a 50 ml round-bottomed flask provided with an argon inlet, KH (37 mg, 0.92 mmol) was suspended in THF (1 ml) and cooled to 0° C. The alcohol 2b from Ex. 1 (433 mg, 0.70 mmol) dissolved in THF (9 ml) was subsequently slowly added dropwise at 0° C. and the reaction mixture was stirred at room temperature for 1 hour. It was once again cooled to 0° C. and MeI (111 mg, 0.78 mmol) was added dropwise. After stirring at 0° C. for 10 minutes and at RT for 10 minutes, the reaction mixture was quenched with saturated $NH_4Cl$ solution (20 ml), the organic phase was separated off and the aqueous phase was extracted with $CH_2Cl_2$ (2×50 ml). The combined organic phases were washed with NaCl solution (20 ml), dried over $MgSO_4$, filtered and the solvent was distilled off on a rotary evaporator. The crude product was purified by column chromatography (n-pentane/$Et_2O$ 1:3). The methyl ether 3b (385 mg, 0.61 mmol, 88%) was obtained as a yellow solid (m.p.: 110–112° C.).

IR (KBr): 3053 (m), 2925 (m), 1636 (m), 1434 (m), 1084 (s), 1044 (s), 813 (m), 746 (s), 697 (s), 498 (s).

$^{31}$P-NMR (CDCl3, 81 MHz): −14.67.

$C_{37}H_{33}FeO_2PS$ (628.55): HR-MS: calc.: 628.1288. found.: 628.

Example 4

Preparation of a Compound of the Formula (4a)

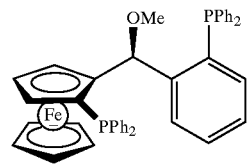

4a

In a 50 ml round-bottomed flask provided with an argon inlet compound 3a from Ex. 2 (155 mg, 0.25 mmol) was dissolved in THF (3 ml) and the solution was cooled to −78° C. t-BuLi (0.31 ml, 0.49 mmol, 1.6 M in hexane) was subsequently slowly added dropwise and the mixture was stirred at −78° C. for 10 minutes. Chlorodiphenylphosphine (0.15 ml, 0.86 mmol) was added dropwise, the cooling bath was removed and the reaction mixture was stirred at room temperature for 30 minutes. After quenching with saturated $NH_4Cl$ solution (20 ml), the organic phase was separated off and the aqueous phase was extracted with diethyl ether (2×50 ml). The combined organic phases were washed with NaCl solution (20 ml), dried over $MgSO_4$, filtered and the solvent was distilled off on a rotary evaporator. The crude product was purified by column chromatography (n-pentane/$Et_2O$ 30:1). The diphosphine 4a (127 mg, 0.19 mmol, 76%) was obtained as a yellow solid (m.p.: 201° C. (decomp.)).

IR (KBr): 3068 (m), 3054 (m), 2924 (w), 1628 (w), 1478 (m), 1434 (s), 1087 (s), 818 (w), 742 (vs), 698 (vs), 498 (s), 488 (s).

$^{31}$P-NMR ($CDCl_3$, 81 MHz): −17.27 (d, J=17.2 Hz), −18.39 (d, J=17.2 Hz). $C_{42}H_{36}FeOP_2$ (674.54): HR-MS: calc.: 674.1591. found.: 674.

Example 5

Preparation of a Compound (5a)

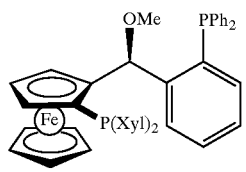

5a

In a 50 ml round-bottomed flask provided with an argon inlet compound 3a from Ex. 2 (180 mg, 0.29 mmol) was dissolved in THF (3 ml) and the solution was cooled to −78° C. t-BuLi (0.36 ml, 0.57 mmol, 1.6 M in hexane) was subsequently slowly added dropwise and the mixture was stirred at −78° C. for 10 minutes. Chlorobis(3,5-dimethylphenyl)phosphine (277 mg, 1.00 mmol) was added dropwise, the cooling bath was removed and the reaction mixture was stirred at room temperature for 30 minutes. After quenching with saturated NH$_4$Cl solution (20 ml), the organic phase was separated off and the aqueous phase was extracted with diethyl ether (2×50 ml). The combined organic phases were washed with NaCl solution (20 ml), dried over MgSO$_4$, filtered and the solvent was distilled off on a rotary evaporator. The crude product was purified by column chromatography (n-pentane/Et$_2$O 20:1). The diphosphine 5a (142 mg, 0.19 mmol, 68%) was obtained as a yellow solid (m.p.: 182° C.).

IR (KBr): 3052 (m), 2922 (m), 2818 (w), 1629 (w), 1434 (m), 1092 (m), 847 (w), 816 (w), 745 (m), 695 (s), 507 (m).

$^{31}$P-NMR (CDCl$_3$, 81 MHz): −18.49 (d, J=23.7 Hz), −19.05 (d, J=23.7 Hz). C$_{46}$H$_{44}$FeOP$_2$ (730.65): HR-MS: calc.: 730.2217. found.: 730.

Example 6

Preparation of a Compound (4b)

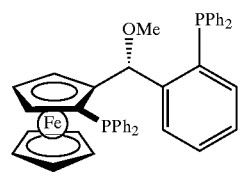

4b

In a 50 ml round-bottomed flask provided with an argon inlet compound 3b from Ex. 3 (298 mg, 0.47 mmol) was dissolved in THF (6 ml) and the solution was cooled to −78° C. t-BuLi (0.59 ml, 0.95 mmol, 1.6 M in hexane) was subsequently slowly added dropwise and the mixture was stirred at −78° C. for 10 minutes. Chlorodiphenylphosphine (0.30 ml, 1.66 mmol) was added dropwise, the cooling bath was removed and the reaction mixture was stirred at room temperature for 30 minutes. After quenching with saturated NH$_4$Cl solution (20 ml), the organic phase was separated off and the aqueous phase was extracted with diethyl ether (2×50 ml). The combined organic phases were washed with NaCl solution (20 ml), dried over MgSO$_4$, filtered and the solvent was distilled off on a rotary evaporator. The crude product was purified by column chromatography (n-pentane/Et$_2$O 20:1). The diphosphine 4b (216 mg, 0.32 mmol, 68%) was obtained as a yellow solid.

IR (KBr): 3068 (m), 3052 (m), 2925 (w), 2816 (w), 1630 (w), 1479 (m), 1434 (s), 1082 (s), 820 (m), 743 (vs), 696 (vs), 501 (s), 486 (s), 456 (m).

$^{31}$P-NMR (CDCl$_3$, 81 MHz): −14.69 (d, J=16.8 Hz), −20.26 (d, J=16.8 Hz). C$_{42}$H$_{36}$FeOP$_2$ (674.54): HR-MS: calc.: 674.1591. found.: 674.

Individual examples of the asymmetric hydrogenation of unsaturated organic compounds using the ligands prepared as described in Examples 1 to 6 are described below.

Example 7

Procedure for the Enantioselective Hydrogenation of methyl(cis)-3-phenyl-2-methylcarboxamido-2-propenoate Preparation of (S)-methyl 2-methylcarboxamido-3-phenyl-propanoate (6)

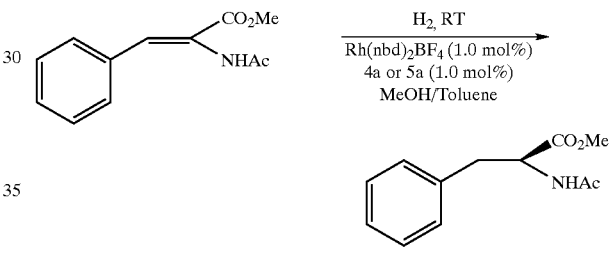

6

In a 50 ml Schlenk vessel, Rh(nbd)$_2$BF$_4$ (3.4 mg, 1 mol %) and the diphosphine ligand (1 mol %) were dissolved in toluene/MeOH (6 ml, 5:1) under argon. After all of the rhodium complex had gone into solution, methyl(cis)-3-phenyl-2-methylcarboxamido-2-propenoate (200 mg, 0.91 mmol) dissolved in MeOH (4 ml) was added. The Schlenk vessel was subsequently connected via a three-way stopcock with a hydrogen balloon and an oil pump and the inert gas atmosphere was replaced by hydrogen. The reaction mixture was stirred at room temperature for the time indicated and the solvent was then distilled off in an oil pump vacuum. The residue was filtered through a short silica gel column (eluent: diethyl ether) and the solvent was distilled off on a rotary evaporator. Compound (S)-6 was obtained as a white solid in quantitative yield.

The enantiomeric excesses achieved by means of the ligands used are shown in Table 1.

TABLE 1

| Ligand* | t [h] | p [bar] | Conversion [%] | ee [%][a] |
|---|---|---|---|---|
| 4a | 1.5 | 1 | 100 | 98.5 (S) |
| 5a | 1.5 | 1 | 100 | 98.7 (S) |
| 4b | 2.0 | 1 | 100 | 94.2 (S) |

[a]Absolute configuration in brackets

The enantiomeric excess was determined by gas chromatography (GC) [column: Chirasil-L-Val (0.12 μm, 25 m×0.22 mm fused silica WCOT) from Chrompack, column prepressure: 83.5 kPa, carrier gas: hydrogen]:

GC (140° C.): tr/min=11.61 (R), 12.50 (S).

$^1$H-NMR (CDCl$_3$, 300 MHz): 7.25–7.18 (m, 3H), 7.04.7.00 (m, 2H), 5.96 (d, J=7.1 Hz, 1H), 4.85–4.78 (m, 1H), 3.65 (s, 3H), 3.11–2.97 (m, 2H), 1.90 (s, 3H).

$^{13}$C-NMR (CDCl$_3$, 75 MHz): 172.07, 169.52, 135.85, 129.18, 128.51, 127.06, 53.10, 52.21, 37.83, 23.02.

Example 8

Procedure for the Enantioselective Hydrogenation of Dimethyl Itaconate

Preparation of Dimethyl 2-methylsuccinate (7)

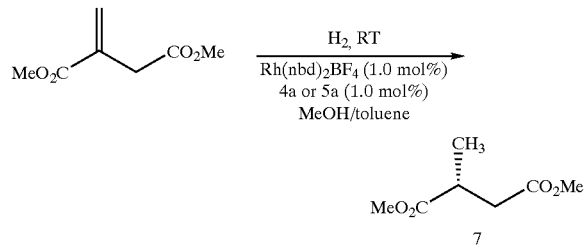

In a 50 ml Schlenk vessel, Rh(nbd)$_2$BF$_4$ (4.7 mg, 1 mol %) and the diphosphine ligand (1 mol %) were dissolved in toluene/MeOH (6 ml, 5:1) under argon. After all of the rhodium complex had gone into solution, dimethyl itaconate (200 mg, 1.26 mmol) dissolved in MeOH (4 ml) was added. The Schlenk vessel was subsequently connected via a three-way stopcock with a hydrogen balloon and an oil pump and the inert gas atmosphere was replaced by hydrogen. The reaction mixture was stirred at room temperature for the time indicated and the solvent was then distilled off on a rotary evaporator. The residue was filtered through a short silica gel column (eluent: diethyl ether). Compound (R)-7 was obtained as a colorless oil in quantitative yield.

The enantiomeric excesses achieved by means of the ligands used are shown in Table 2.

TABLE 2

| Ligand | t [h] | p [bar] | Conversion [%] | ee [%]$^a$ |
|---|---|---|---|---|
| 4a | 0.5 | 1 | 100 | 98.1 (R) |
| 5a | 1.0 | 1 | 100 | 89.8 (R) |
| 4b | 2.5 | 1 | 100 | Low |

$^a$Absolute configuration in brackets

The enantiomeric excess was determined by high-performance liquid chromatography (HPLC) (HPLC unit from Dionex with automatic sample introduction and UV-VIS diode array detector, column: OD from Daicel Chemical Industries, eluent: n-heptane/i-PrOH 95:5, flow: 0.6 ml/min, detected wavelength: 215 nm):

HPLC (OD, 5% i-PrOH, 0.6 ml/min, 215 nm): tr/min=10.37 (R), 17.93 (S).

Example 9

Procedure for the enantioselective hydrogenation of methyl 2-acetoxyacrylate

Preparation of (S)-methyl 2-methylcarbonyloxypropanoate (8)

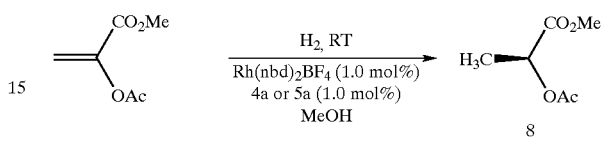

In a 50 ml Schlenk vessel, Rh(nbd)$_2$BF$_4$ (5.2 mg, 1 mol %) and the diphosphine ligand (1 mol %) were dissolved in MeOH (10 ml) under argon. After all of the rhodium complex had gone into solution, methyl 2-acetoxyacrylate (200 mg, 1.39 mmol) was added. The Schienk vessel was subsequently connected via a three-way stopcock with a hydrogen balloon and an oil pump and the inert gas atmosphere was replaced by hydrogen. The reaction mixture was stirred at room temperature for 20 h and the solvent was then distilled off in an oil pump vacuum. The residue was purified by bulb tube distillation. The ester (S)-8 was obtained as a colorless oil in quantitative yield.

The enantiomeric excesses achieved by means of the ligands used are shown in Table 3.

TABLE 3

| Ligand | t [h] | p [bar] | Conversion [%] | ee [%]$^a$ |
|---|---|---|---|---|
| 4a | 20 | 10 | 100 | 94.9 (S) |
| 5a | 20 | 10 | 100 | 97.3 (S) |
| 5a | 20 | 1 | 100 | 98.5 (S) |
| 4b | 20 | 10 | 100 | 79.8 (S) |

$^a$Absolute configuration in brackets

The enantiomeric excess was determined by high-performance liquid chromatography (HPLC) (HPLC unit from Dionex with automatic sample introduction and UV-VIS diode array detector, column: OD-H from Daicel Chemical Industries, eluent: n-heptane/i-PrOH 99:1, flow: 0.6 ml/min, detected wavelength: 215 nm):

HPLC (OD-H, 1% i-PrOH, 0.6 ml/min, 215 nm): tr/min=13.86 (S), 16.14 (R).

$^1$H-NMR (CDCl$_3$, 300 MHz): 4.99 (q, J=7.1 Hz, 1H), 3.65 (s, 3H), 2.03 (s, 3H), 1.39 (d, J=7.1 Hz, 3H).

$^{13}$C-NMR (CDCl$_3$, 75 MHz): 171.26, 170.33, 68.46, 52.25, 20.58, 16.84.

As can be seen from Tables 1 to 3, the asymmetric hydrogenation using the ligands 4a and 5a which are both S$_{fc}$,S enantiomers proceeds more selectively than when using the corresponding S$_{fc}$,R enantiomer 4b.

The invention claimed is:

1. A ferrocenyl ligand of the general formula (II)

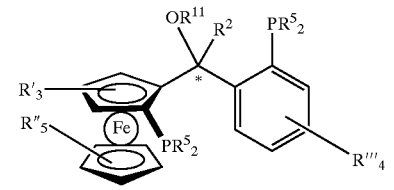
(IIa)

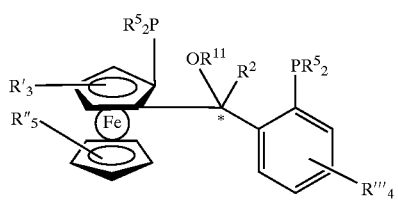
(IIb)

wherein
the $S_{fc},S$ enantiomer of the formula (IIIa) is present in excess in the stereoisomer mixture (IIa) or the $R_{fc},R$ enantiomer of the formula (IIIb) is present in excess in the stereoisomer mixture (IIb)

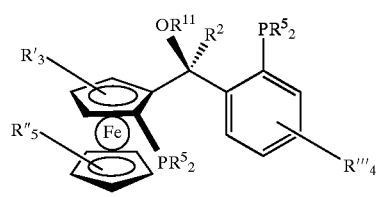
(IIIa)

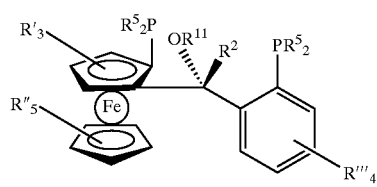
(IIIb)

and
R' and R" are radicals which can be independently selected from the group consisting of H, $CH_3$ and mixtures thereof or can be a linker which connects the ligands to a polymeric support and the radicals,
R'" are radicals which can be independently selected from the group consisting of H, $(C_1-C_4)$-alkyl and mixtures thereof and the radicals,
$R^5$ can be, independently of one another, radicals selected from the group consisting of $C_6$-aryl, $C_5-C_6$-cycloalkyl, adamantyl, $C_1-C_4$-alkyl and mixtures thereof, where the radicals $R^5$ may bear one or more $(C_1-C_4)$-alkyl substituents and
$R^2$ is hydrogen or a $(C_1-C_4)$-alkyl radical and
$R^{11}$ is a $(C_1-C_4)$-alkyl radical.

2. The ferrocenyl ligand as claimed in claim 1, wherein
$R^{11}$ is a methyl radical and/or
$R^2$ is H or a methyl radical and/or
R', R", R'" are hydrogen radicals and/or the radicals $R^5$ are, independently of one another, phenyl, tolyl or xylyl radicals.

3. The ferrocenyl ligand as claimed in either claim 1 wherein the $S_{fc},S$ enantiomer or the $R_{fc},R$ enantiomer is present in the stereoisomer mixture in a proportion of over 60%.

4. The ferrocenyl ligand as claimed claim 1 wherein the ligand is present as $S_{fc},S$ enantiomer or as $R_{fc},R$ enantiomer having a purity of over 99%.

5. A process for preparing a complex comprising forming the complex with the ferrocenyl ligands as claimed in claim 1.

6. A process for preparing a complex comprising forming the complex with the ferrocenyl ligands as claimed in claim 1 with at least one metal, metal salt or metal precomplex selected from the group consisting of transition group 7 and 8.

7. A process for the asymmetric hydrogenation or hydroformylation of unsaturated organic compounds comprising hydrogenating or hydroformylating unsaturated organic compounds in the presence of the ferrocenyl ligands as claimed in claim 1.

8. A process for the asymmetric hydrogenation of C=C, C=O or C=N bonds comprising hydrogenating C=C, C=O or C=N bonds in the presence of the ferrocenyl ligands as claimed in claim 1.

9. A process for preparing ferrocenyl ligands of the general formula (II)

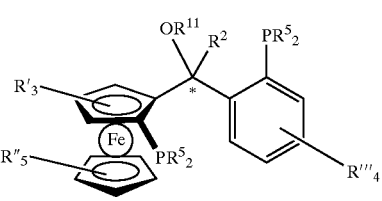
(IIa)

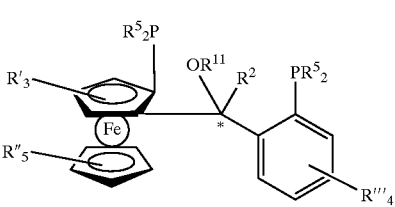
(IIb)

where the $S_{fc},S$ enantiomer of the formula (IIIa) is present in excess in the mixture (IIa) or the $R_{fc},R$ enantiomer of the formula (IIIb) is present in excess in the mixture (IIb)

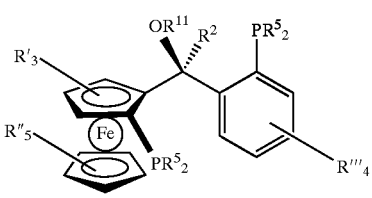
(IIIa)

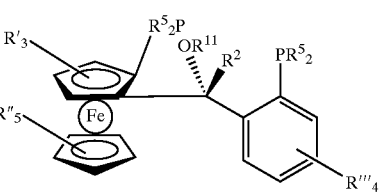
(IIIb)

and

R' and R" can each be, independently of one another, a substituent selected from the group consisting of H, $(C_1-C_4)$-alkyl and mixtures thereof or a linker which connects the ligands to a polymeric support and the radicals R''' are radicals which can be independently selected from the group consisting of H, $(C_1-C_{18})$-alkyl, $(C_1-C_{18})$-alkoxy, $(C_1-C_{18})$-acyloxy, $(C_6-C_{14})$-aryl, $(C_3-C_{18})$-heteroaryl, $(C_2-C_{17})$-heteroalkyl, $(C_3-C_8)$-cycloalkyl, $(C_2-C_{10})$-alkenyl and mixtures thereof, where two adjacent radicals may also be joined to one another to form a ring system, and the radicals $R^5$ can each be, independently of one another, selected from the group consisting of $(C_1-C_{18})$-alkyl, $(C_6-C_{18})$-aryl, $(C_6-C_{18})$-aryl-$(C_1-C_8)$-alkyl, $(C_3-C_{18})$-heteroaryl, $(C_3-C_{18})$-heteroaryl-$C_1-C_8)$-alkyl, $(C_2-C_{17})$-heteroalkyl, $(C_3-C_8)$-cycloalkyl, $(C_3-C_8)$-cycloalkyl-$(C_1-C_8)$-alkyl, $(C_2-C_{10})$-alkenyl radicals and mixtures thereof which may bear one or more $(C_1-C_4)$-alkyl substituents and the radical $R^2$ is H or a $(C_1-C_8)$-alkyl radical, $(C_6-C_{18})$-aryl, $(C_6-C_{18})$-aryl-$(C_1-C_8)$-alkyl radical and the radical $R^{11}$ can be a $(C_1-C_{18})$-alkyl, $(C_6-C_{18})$-aryl, $(C_6-C_{18})$-aryl-$(C_1-C_8)$-alkyl radical, which comprises the process steps:

a) coupling of a chiral ferrocenyl sulfoxide with an aromatic aldehyde of the formula (IV),

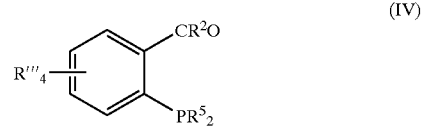

with the chiral ferrocenyl sulfoxide being lithiated in the presence of a lithium base and the coupling of the aromatic aldehyde subsequently being carried out by transmetallation in the presence of a metal catalyst of transition group 8, b) coupling of the free OH group on the chiral center of the reaction product from step a) with an organic radical $R^{11}$ by addition of the corresponding halide $R^{11}$Hal in the presence of an alkali metal hydride and c) replacement of the sulfoxide group of the reaction product from step b) in the presence of a strong lithium base by a phosphorus halide of the formula HalPR$^5_2$.

10. The process as claimed in claim 9, wherein the diastereomers obtained from step a) and/or the diastereomers from step b) are separated prior to being reacted further.

* * * * *